United States Patent [19]

Brinkmann et al.

[11] Patent Number: 5,336,602
[45] Date of Patent: Aug. 9, 1994

[54] EXPRESSION ENHANCER AND USE THEREOF TO INCREASE THE YIELD IN THE EXPRESSION OF RECOMBINANT GENES

[75] Inventors: Ulrich Brinkmann, Hamm; Ralf Mattes, Stuttgart; Peter Buckel, Bernried, all of Fed. Rep. of Germany

[73] Assignee: Boehringer Mannheim GmbH, Mannheim-Waldhof, Fed. Rep. of Germany

[21] Appl. No.: 7,405

[22] Filed: Jan. 22, 1993

Related U.S. Application Data

[63] Continuation of Ser. No. 435,358, Nov. 13, 1989, abandoned.

[30] Foreign Application Priority Data

Nov. 11, 1988 [DE] Fed. Rep. of Germany ....... 3838377

[51] Int. Cl.$^5$ .................. C12P 21/02; C12N 15/67
[52] U.S. Cl. .................. 435/69.1; 435/172.3; 435/215; 435/226; 435/252.33; 435/320.1; 536/24.1; 935/44
[58] Field of Search .............. 435/252.33, 69.6, 320.1, 435/69.1, 172.3, 226; 536/23.1, 24.1

[56] References Cited

PUBLICATIONS

Garcia et al., *Cell* v. 45, 1986, pp. 453–459.
Winnacker, *From Genes to Clones*, 1987, VCH, New York, pp. 276–279.
Pennica et al., *Nature*, v. 301, 1983, pp. 214–221.

*Primary Examiner*—Richard A. Schwartz
*Assistant Examiner*—James Ketter
*Attorney, Agent, or Firm*—Felfe & Lynch

[57] ABSTRACT

An expression enhancer has a DNA sequence which is capable of forming a t-RNA clover-leaf structure after transcription and hybridizes in that region of the DNA which, after transcription, forms the anticodon loop in the clover-leaf structure with an oligonucleotide with the sequence 5'-GACTTAGAAGGTCGTT-3' or its complementary sequence (5'-AACGACCTT-CTAAGTC-3'). It can be used to increase the yield in the expression of a recombinant gene by transformation of suitable host cells with an expression vector containing the recombinant gene, whereby it is likewise introduced into the host cells in a form capable of expression and expressed.

7 Claims, No Drawings

EXPRESSION ENHANCER AND USE THEREOF TO INCREASE THE YIELD IN THE EXPRESSION OF RECOMBINANT GENES

This application is a continuation of application Ser. No. 07/435,358, filed Nov. 13, 1989, now abandoned.

The invention concerns an expression enhancer and its use to increase the yield in the expression of a recombinant gene by transformation of suitable host cells with an expression vector containing the recombinant gene.

In the expression of recombinant genes and above all eukaryotic genes in E. coli one is often confronted by the problem of poor expression of the desired gene. Researchers who are active in this field attribute this to different causes, including low fermentation rate of E. coli cells transformed with particular recombinant genes. Although these cells do sometimes express the recombinant gene quite well, they grow poorly so that only a small biomass is obtained and thus only a low yield of the desired gene is product obtained. The object of the present invention is therefore to provide a process and a means to increase the yield of a desired gene product when expressed in E. coli.

This object is achieved according to the present invention by an expression enhancer comprising a DNA sequence which is transcribed into RNA having a clover leaf like structure containing an anticodon loop, wherein a portion of said DNA sequence which is transcribed into said anticodon loop hybridizes with an oligonucleotide having at least a nucleotide sequence comprising 5'-GACTTAGAAGGTCGTT-3' or 5'-AACGACCTTCTAAGTC-3'. The clover-leaf like structure of t-RNA molecules is effected by base pairing in particular regions of the single stranded RNA molecules, whereby particular homologies occur in all t-RNA molecules. In each of these clover-leaf structures one finds a left loop, the so-called dihydrouridine loop, a second loop, the so-called anticodon loop which can enter into base-pairing with a complementary triplet on m-RNA and thus determines the specificity of the t-RNA, and a loop situated on the right, the so-called pseudouridine loop. Between the anticodon loop and the pseudouridine loop there is often an extra loop which is a variable. The expression enhancer according to the present invention has a DNA structure such that after transcription its RNA can form such a clover-leaf structure. Thus, the invention encompasses both natural and synthetic sequences of DNA which, when transcribed, result in products (RNA) having the clover leak like structure referred to supra. Also encompassed are sequences of DNA which contain this so-called "expression enhancer" sequence as a part of their total sequence. It is characteristic of the expression enhancer according to the present invention that it hybridizes with the above mentioned oligonucleotide at the anticodon loop. In a preferred embodiment of the invention the expression enhancer hybridizes with an oligonucleotide with the sequence 5'-CACGACTTAGAAGGTCGTTG-3' or its complementary sequence (5'-CAACGACCTTCTAAGTCGTG-3').

Such an expression enhancer DNA can be produced synthetically and can be isolated from E. coli cells. In a preferred embodiment of the invention, to produce an expression enhancer a DNA library of chromosomal E. coli DNA partially digested with PstI is set up in a suitable vector, E. coli cells are co-transfected with the gene bank vectors and an expression vector which contains a recombinant gene which when expressed, causes the E. coli cells grow to poorly (whereby the expression "grow poorly" means, within the scope of the present invention, that the cells which expresses the recombinant gene alone grow more poorly than cells which also expresses the expression enhancer), these cells are subsequently selected, induced and cultivated and clones are isolated which have grown to large colonies and from these clones the gene bank vectors are isolated. The presence of the expression enhancer can be checked by hybridization with an oligonucleotide with the sequence 5'-GACTTAGAAGGTCGTT-3' or its complementary sequence (5'-AACGACCTTCTAAGTC-3'). In a particularly preferred embodiment of the invention an oligonucleotide with the sequence 5'-CACGACTTAGAAGGTCGTTG-3' or its complementary oligonucleotide (5'-CAACGACCTTCTAAGTCGTG-3') is used.

The preferred production process according to the present invention can be carried out with expression vectors which contain a recombinant gene which when expressed in E. coli causes the cells to only grow poorly. For this an inducible expression vector is preferably used so that until inducted normal fermentation of the E. coli cells takes place. After induction those clones grow to form large colonies which contain a gene bank vector which in turn contains an expression enhancer according to the present invention. This can be checked by hybridization with an oligonucleotide with the above mentioned sequence. The enhancer can then be isolated from the clones containing the gene bank vector which in turn contains the expression enhancer by digestion with the restriction enzymes used to produce the gene bank.

In a preferred embodiment of the invention it is preferable to use a t-PA expression plasmid. It is especially preferred to use the plasmid pUBS98.sl as the expression vector (see Example 3).

The inducible expression plasmid used according to the present invention is preferably induced by isopropyl-$\beta$-D-thiogalactopyranoside, preferably in an amount of from 5 to 20 mmol/l.

To produce the gene bank, the vector pACYC177, DSM 3693P, is preferred.

A further embodiment of the invention is the use of the expression enhancer according to the present invention to increase the yield when expressing a recombinant gene by tranformation of E. coli cells with an expression vector containing the recombinant gene, whereby the expression enhancer is likewise introduced into the host cells in a form which can be expressed and its expression is effected before or simultaneously with that of the expression vector.

In a preferred embodiment of the invention an expression enhancer is incorporated into the expression vector containing the recombinant gene. This is carried out according to the present invention such that the expression enhancer is either under the control of its own separate promoter or is controlled together with the recombinant gene by the same promoter.

In another preferred embodiment of the present invention the expression vector is incorporated into a vector compatible with the expression vector containing the recombinant gene. In accordance with the invention a compatible vector is understood as a vector which has a different origin of replication from the expression vector. This enables simultaneous replication and transcription of both plasmids in one cell.

Preferably the plasmid pUBS100 is used as the vector containing the expression enhancer, and a vector which is compatible with it, e.g. the plasmid pUBS98.sl which expresses t-PA, is used as the expression vector containing the recombinant gene. In a preferred embodiment of the invention one expresses as the recombinant gene, the gene or the c-DNA for t-PA or a t-PA derivative, urokinase or a HIV-protein.

The expression of the expression enhancer can take place according to the invention before or simultaneously with the expression vector containing the recombinant gene, whereby the expression should not occur too long before that of the expression vector so that the gene product of the expression enhancer is not degraded to a significant extent by nucleases in the host cells. Therefore according to the present invention it is preferable to effect the expression simultaneously with that of the expression vector. This is carried out in an especially preferred way by constitutive expression or induction. For this the expression enhancer can, according to the present invention, be for example under the control of an inducible promoter preferably, the lac-promoter.

The invention is further elucidated by the following examples.

EXAMPLE 1

Cloning and selection of an expression enhancer:

A gene bank of *E. coli* DNA partially digested with the restriction enzyme PstI was set up in pACYC177, DSM 3693P (Chang and Cohen, J- Bacteriol. 134 (1978), 1141–1156) using well known molecular biological methods summarized inter alia in Winnacker E. L., Gene und Klone, VCH-Verlag 1985. For this pA-CYC177-plasmid-DNA which had been cut with PstI was ligated with chromosomal *E. coli* DNA partially digested with PstI. Clones which contain an insert in the PstI site of pACYC177 can be identified by ampicillin sensitivity as well as by the molecular weight which is increased according to the length of the insert. The plasmid DNA of such clones can be separated and isolated from plasmid DNA without an insert by gel electrophoresis/gel elution. The plasmid pUBS100 was isolated from this gene bank by co-transformation of the gene bank plasmids with the t-PA expression plasmid pUBS98.sl (for its production see Example 3) and selected on LB-kanamycin/ampicillin plates which contained 10 mmol/l IPTG (isopropyl-β-D-thiogalactopyranoside). This plasmid pUBS100 contains a portion of chromosomal *E. coli* DNA about 3000 bases long which has the effect that the *E. coli* cells, DSM 3689, which carry the plasmid pUBS100 and the expression plasmid pUBS98.sl and which produce t-PA by IPTG induction, can grow into large colonies after induction compared to *E. coli* cells with pUBS98.sl and pACYC177.

EXAMPLE 2

Expression of t-PA in *E. coli* by co-transformation with a plasmid containing the expression enhancer.

In this example the plasmid pUBS100 was used as the plasmid containing the expression enhancer. The expression in *E. coli*, DSM 3689, co-transformed with pUBS100 and the t-PA expression plasmid pUBS98.sl was compared with the rate of expression in the same host cells transformed with plasmid pUBS98.sl alone. Furthermore the rate of expression was compared with that of the plasmid pePa98.1 (DE 36 13 401) in the same strain. The results of these comparisons are shown in Table 1. In addition the expression of t-PA was examined using a plasmid which contains the expression enhancer and the t-PA-gene that is namely the plasmid pUBS98.sky, DSM 4898. The results of this are also shown in Table 1.

TABLE 1

| *E. coli*, DSM 3689 | % intact t-PA/ total protein | Vitality |
|---|---|---|
| +pePa98.1 | 3% | limited |
| +pUBS98.sl | 10% | very poor |
| +pUBS98.sl + pUBS100 | 30% | very good |
| +pUBS98.sky | 30% | very good |

From the results shown in Table 1 it can be clearly seen that the rate of expression of t-PA expressed in *E. coli* cells which contain, in addition the expression enhancer, is significantly increased in comparison to cells which do not contain the expression enhancer. This correlates with the vitality of the clones obtained.

EXAMPLE 3

The plasmid pePa98.1 (EP-A-242 836) was used as the starting plasmid for the construction of plasmid pUBS98.sl. The 3'-untranslated region of the t-PA-cDNA in this plasmid, which is approximately 400 base pairs long, was shortened to approximately 40 base pairs by deletion of a XhoII-fragment of 361 base pairs. The resulting plasmid was named pePa126.1 and can for example be distinguished from pePa98.1 in that when these plasmids are twice digested with the restriction endonucleases BamHI and HindIII two fragments with lengths of 2234 base pairs and 4372 base pairs can be detected with plasmid pePa98.1 compared to two fragments with lengths of 1873 base pairs and 4372 base pairs with plasmid pePa126.1. This plasmid pePa126.1 was linearized at the single HindIII cleavage site and the protruding ends were completely filled in using Klenow enzyme and dNTP's. In addition an EcoR1 fragment of 472 base pairs was also isolated from the plasmid pePa126.1 and treated with S1-nuclease. The plasmid pUBS98.sl was obtained by ligation of both fragments from the plasmid pePa126.1. pUBS98.sl can be distinguished from pePa126.1 by restriction analysis: pePa126.1 DNA digested by BanII is defined by fragments with lengths of 1175 base pairs, 393 base pairs, 14 base pairs, 165 base pairs and 4560 base pairs; pUBS98.sl-DNA is characterized in that BanII fragments have lengths of approximately 1175 base pairs, 393 base pairs, 14 base pairs, 165 base pairs, 470 base pairs and 4540 base pairs.

We claim:

1. Method for increasing yield of an arginine containing protein coded for by a gene, comprising:
    (a) transforming an *Escherichia coli* host cell with
        (1) a DNA sequence which codes for an arginine tRNA molecule wherein a segment of said DNA sequence
            (i) is complementary to an oligonucleotide having the sequence 5'-TTAGAAG-3', and
            (ii) encodes an anticodon loop of said arginine tRNA molecule, and
        (2) an expression vector comprising said gene coding for a protein, and
    (b) cultivating said *Escherichia coli* host cell under conditions favoring expression of said protein wherein expression of said protein is enhanced as compared to expression in the absence of said DNA sequence which codes for said arginine tRNA in said *Escherichia coli* cultivated under identical conditions.

2. Method of claim 1, wherein said DNA sequence is incorporated into said expression vector.

3. Method of claim 1, wherein said DNA sequence is incorporated into a second vector which is compatible with said expression vector.

4. Method of claim 3, wherein said second vector contains said DNA sequence and is plasmid pUBS 100.

5. Method of claim 1, wherein said protein is t-PA, a t-PA derivative, urokinase, or a human immunodeficiency virus protein.

6. Method of claim 4, wherein said expression vector is plasmid pUBS 98.sl.

7. Method of claim 1, wherein said segment of said DNA sequence is complementary to an oligonucleotide having the sequence 5'-GACTTAGAAGGTCGTT-3'.

* * * * *